United States Patent
Kaufman et al.

(12)

(10) Patent No.: US 6,350,769 B1
(45) Date of Patent: Feb. 26, 2002

(54) GABA ALPHA RECEPTORS MEDIATE INHIBITION OF T CELL RESPONSES

(75) Inventors: Daniel L. Kaufman, Santa Monica; Jide Tian, Los Angeles, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/513,259

(22) Filed: Feb. 24, 2000

Related U.S. Application Data

(60) Provisional application No. 60/121,352, filed on Feb. 24, 1999.

(51) Int. Cl.⁷ .................. A61K 31/47; A61K 31/56; A61K 31/55; A61K 31/50; A61K 31/195
(52) U.S. Cl. .................. 514/380; 514/182; 514/221; 514/249; 514/567
(58) Field of Search .................. 514/380, 567, 514/249, 182, 221

(56) References Cited

U.S. PATENT DOCUMENTS

| | | | | |
|---|---|---|---|---|
| 5,637,617 A | * | 6/1997 | Woodward et al. | 514/567 |
| 5,723,462 A | * | 3/1998 | Albaugh et al. | 514/249 |
| 5,925,630 A | * | 7/1999 | Upasani et al. | 514/182 |

OTHER PUBLICATIONS

Devoino et al., "Immunomodulating effect of activators and blockers of the GABA–receptor–ionophore complex", Farmakol. Toksikol. (Moscow) (1988), 51(3), pp. 78–80 (abstract).*

Bergeret et al. (1998) GABA modulates cytotoxicity of immunocompetent cells expressing $GABA_A$ receptor subunits Biomed. Pharmacother. 52(5): 214–219.

Defeudis et al. (1998) Muscimol and central nervous system gamma–aminobutyric amino acid receptors: studies with ligand binding techniques (1986) in Receptors, vol. 3, Eds. Conn, P.M., Publ. Academic, Orlando, FL.

Ratnikov et al. (1982) Effect of GABA–ergic substances on humoral immunity Biull.Eksp.Biol.Med. 94:56–58.

International Search Report mailed May 30, 2000 for International Application No. PCT/US00/04921.

* cited by examiner

Primary Examiner—Kevin E. Weddington
(74) Attorney, Agent, or Firm—Townsend & Townsend & Crew LLP

(57) ABSTRACT

The present invention provides new methods for modulating immune responses. The methods are based on the discovery that $GABA_A$ receptors are present on peripheral lymphocytes. Thus, GABA agonists and antagonists can be used to modulate immune responses.

9 Claims, 8 Drawing Sheets

GABA ALPHA RECEPTORS MEDIATE INHIBITION OF T CELL RESPONSES

CROSS-REFERENCES TO RELATED APPLICATIONS

The present application claims priority to the U.S. Provisional Application No. 60/121,352 filed Feb. 24, 1999, herein incorporated by reference in its entirety.

STATEMENT AS TO RIGHTS TO INVENTIONS MADE UNDER FEDERALLY SPONSORED RESEARCH AND DEVELOPMENT

This invention was made with Government support under Grant Nos. A143712 awarded by the National Institutes of Health and 196061 awarded by the Juvenile Diabetes Foundation International Research Award. The Government has certain rights in this invention.

BACKGROUND OF THE INVENTION

Many of the cells of the immune system express receptors for neuroactive molecules which modulate immune system function, creating a link between the nervous and immune systems (Nio et al. (1993) *J Immunol.* 150:5281–5288; Torcia et al. (1996) *Cell* 85:345–356).

γ-Aminobutyric acid (GABA) is a ubiquitous inhibitory neurotransmitter in the central nervous system (CNS; reviewed in Erdo and Wolff (1990) *J. Neurochem.* 54:363–372; Olsen and Tobin (1990) *Faseb J.* 4:1469–1480; Kaufmnan and Tobin (1993) *Trends Pahrmacol. Sci.* 14:107–109; Macdonald and Olsen (1994) *Ann. Rev. Neurosc.* 17:569–602; and Luddens et al. (1995) *Neuropharmacology* 34:245–254). GABA is synthesized from glutamic acid by the enzyme glutamate decarboxylase (GAD; reviewed in Erlander et al. (1991) *Neuron* 7:91–100). Outside of the brain, GAD and GABA receptors have been reported in the pancreatic islets, the gastrointestinal tract, ovaries and adrenal medulla (Erdo and Wolff (1990), supra).

There are at least two types of neuronal GABA receptors, $GABA_A$ and $GABA_B$. $GABA_A$ receptors are ligand-gated ion channels which respond to GABA by opening their integral $Cl^-$ channel (Olsen and Tobin (1990); Macdonald and Olsen (1994); Luddens et al. (1995); all supra). Pharmacologically, muscimol acts as an agonist for $GABA_A$ receptors and anxiolytic benzodiazepines as well as anesthetic agents (such as pentobarbital) potentiate the opening of the $GABA_A$-$Cl^-$ channel. Bicuculline and RU5315 antagonize $GABA_A$ receptor function and picrotoxin blocks the $GABA_A$ receptor $Cl^-$ channel (Macdonald and Olsen (1994); and Luddens et al. (1995); both supra). In contrast, $GABA_B$ receptors are coupled to $Ca^{2+}$ or $K^+$ channels via GTP-binding proteins and are selectively activated by baclofen (Bowery (1993) *Annu. Rev. Pharmacol. Toxicol.* 33:109–147). $GABA_B$ receptors are insensitive to bicuculline and picrotoxin. The administration of GABA or its agonists peripherally inhibits antibody production and modulates macrophage phagocytosis in vivo (Ratnikov et al. (1982) *Biull. Eksp. Biol. Med.* 94:56–58; and Frangulyan et al. (1986) "Influence of neuroactive amino acids on some indexes of natural immunity" In: Neurohumoral regulation of Immune Homeostasis, Leningrad, Russia).

Many diseases, including allergies and autoimmune diseases, as well as graft rejection, result from a deleterious immune response. For example, more than 30 autoimmune diseases are presently known; these include many which have received much public attention, including myasthenia gravis (MG) and multiple sclerosis (MS). Characteristic of these diseases is the attack by the immune system on the tissues of the victim—these tissue antigens being non-immunogenic in non-diseased individuals because of their tolerance of the immune system to "self." In autoimmune diseases, this tolerance apparently is compromised, and the tissue of the afflicted subject is treated as an invader—i.e., the immune system sets about destroying this presumed foreign target. Furthermore, graft rejection results from the activation of T lymphocytes and allergic reaction are also due to an exacerbated immune response.

Alternatively, enhancing immune responses is useful for treating a number of diseases and infections. In addition, redirecting the immune response can result in a more efficient immunity against certain diseases. For example, a viral infection will be more efficiently eliminated if the immune response can be redirected from a predominantly antibody response to a protective Th1 cell-mediated response.

There is, therefore, a need in the art for methods to modulate the immune system to treat a variety of diseases. The present invention addresses these and other needs.

SUMMARY OF THE INVENTION

The present invention provides methods of modulating an immune response in a patient. The methods comprise administering an immunomodulatory amount of a compound that binds the GABA binding site within a $GABA_A$ receptor. The compounds are preferably administered orally, transdermally, intravenously, subcutaneously, or using a pump. The compound used in the method can be either an agonist or an antagonist of GABA. In one embodiment, the methods of the invention are used to down-regulate an immune response and the compound is a GABA agonist. These methods are particularly useful in treating diseases which involve a deleterious immune response such as autoimmune disease, allergy, and graft rejection. The methods may further comprise administering a GABA potentiator. In one embodiment, the potentiator binds to the benzodiazepine binding site within a $GABA_A$ receptor. In another embodiment, the potentiator binds to the barbiturate binding site within a $GABA_A$ receptor. In yet another embodiment the potentiator binds to the steroid binding site within a $GABA_A$ receptor.

The invention also provides methods in which the compound that binds the $GABA_A$ receptor is a GABA antagonist. These methods are used to enhance an immune response. The methods are particularly useful in enhancing a Th1-mediated immune response. Such methods are useful, for example, in enhancing immune response against certain pathogens such as viruses.

DESCRIPTION OF THE SPECIFIC EMBODIMENTS

I. INTRODUCTION

Figure 1:
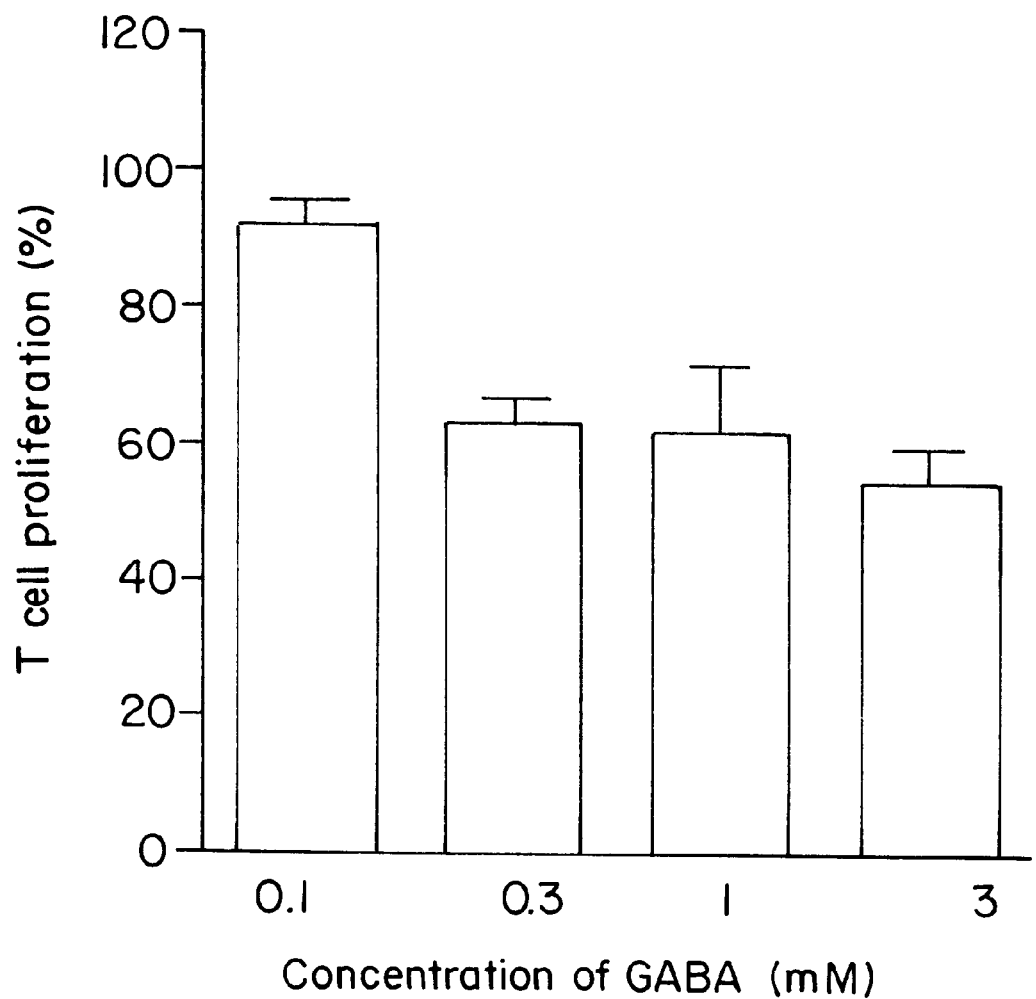
FIG. 1 shows that GABA inhibits anti-CD3 stimulated splenic T cell responses. Splenic mononuclear cells ($3 \times 10^5$/well) from female Balb/c mice were incubated with anti-CD3 in the presence or absence of the indicated concentrations of GABA for 48 hours (in triplicate). During the last 8 hours of incubation, $^3$H-thymidine (1 μCi/well) was added into each well to determine T cell proliferation. The data are presented as the per cent $^3$H-thymidine incorporation relative to control anti-CD3 stimulated cells in the absence of GABA (201,840–209,725 cpm). The background level of $^3$H-thymidine incorporation in medium alone was 1,965–2,400 cpm. Groups of 5–6 mice were tested in two independent experiments.

The present invention is based, at least in part, on the discovery of the presence of $GABA_A$ receptors on immunocompetent cells. This observation leads to the use of agonists, potentiators and antagonists of GABA to modulate or mediate the immuno-suppressive effects of GABA, and in particular Th1 cell-mediated effects. $GABA_A$ receptors can be targeted by a variety of compounds in order to modulate the immune response. The present invention provides compositions and methods to treat a variety of immune diseases by modulating the activity of these peripheral $GABA_A$ receptors. The present invention provides, in particular, methods to inhibit the immune system for treating autoimmune diseases, allergies, and graft rejection, as well as methods to enhance the immune system to treat, for example, microbial infections.

II. COMPOUNDS OF THE INVENTION

The functional $GABA_A$ receptors present on T cells are pharmacologically similar to their central nervous system counterparts and can be modulated pharmacologically using known compounds that bind $GABA_A$ receptors on cells in the central nervous system.

$GABA_A$ receptors are pentamers consisting of various combinations of alpha, beta and gamma subunits that assemble to form a functional chloride channel. $GABA_A$ receptors comprise at least four different binding sites: a GABA binding site, a benzodiazepine binding site, a barbiturate binding site and a steroid binding site (see, e.g., Kardos (1999) *Neurochem. Int.* 34:353–358; De Blas (1996) *Mol. Neurobiol.* 12:55–71; and Smith and Olsen (1995) *Trends Pharmacol. Sci.* 16:162–168).

As used herein, a "compound that binds a $GABA_A$ receptor" is a compound that modulates responses mediated by the receptor. Such compounds may bind any of the binding sites in the receptor and modulate the responses mediated by the receptor independently or in combination with GABA (or with a GABA analog). Such compounds may compete directly with GABA for binding site to the receptor. Alternatively, if GABA and the compound bind the receptor simultaneously, the compound may act non-competitively.

"A compound that binds the GABA binding site" within the GABA$_A$ receptor is typically the topographical equivalent of GABA and will compete directly for the binding site on the GABA receptor. Standard assays to determine whether a compound is capable of competing directly with GABA for binding to the GABA binding site within the GABA receptor are well known to those of skill in the art. Such compounds modulate the responses mediated by the receptor, e.g., T cell proliferation as determined according to standard assays described below.

A compound that binds the GABA receptor may be either agonist, a potentiator or antagonist. As used herein, "GABA agonists" are compounds which bind to the GABA binding site within the GABA receptor and initiate a physiological response similar to that of the natural ligand, e.g., T cell proliferation as determined according to standard assays described below. A number of GABA agonists are known as described below. "Potentiators" are compounds that bind the GABA receptor simultaneously to GABA (i.e., predominantly at a different site) and enhance the effect of GABA. In the context of the present invention, "antagonists" are compounds which reverse the physiological effect of a ligand or exclude binding of the ligand to the receptor. Such compounds may compete directly or indirectly with GABA for binding to the receptor. A non-competitive inhibitor acts by decreasing or inhibiting the subsequent physiological effects of receptor-ligand interactions rather than by diminishing the proportion of ligand molecules bound to the receptor. Such non-competitive inhibitors typically bind the GABA receptor at a different site from GABA.

A variety of compounds have been shown to bind different sites of the GABA receptor and to mimic, potentiate or inhibit the action of the GABA neurotransmitter (Mehta and Ticku (1999) *Brain Res. Rev.* 29:196–217). Some compounds can act both as potentiators and as agonists of the effects of GABA (WO 99/29319). The pharmacological activity of a given compound (WO 99/43661) and/or the dosage required to obtain the desired effect on T cell proliferation can be easily determined using standard assays well known to those of skill in the art. In preferred embodiments, the compounds of the present invention modulate the effect of GABA through the GABA$_A$ receptor. In preferred embodiments, the compounds of the present invention bind the GABA binding site within the GABA$_A$ receptor and act as agonists.

In the context of the present invention, an "immunomodulatory amount" is an amount of compound that is capable of modulating the immune response mediated by a peripheral GABA receptor. The route of administration for an immunomodulatory amount can be any route other than direct administration to the central nervous system, and includes, e.g., intravenous administration, oral administration, transdermal administration, subcutaneous administration, using a pump, etc.

A. Agonists

Numerous compounds that mimic the effects of GABA by binding predominantly to the GABA binding site within the GABA$_A$ receptor have been identified. Such agonists include, but are not limited to, e.g., muscimol, homotaurine, isoguvacine, trans-aminocyclopentane-3-carboxylic acid, trans-amino-4-crotonic acid, THIP, imidazole acetic acid, β-guanidino-propionic acid, homohypotaurine, 3-aminopropanesulfonic acid, kojic amine, cis-3-[(aminoiminomethyl)thio]propenoic acid, homo-β-proline, etc. (see, e.g., Olsen et al. (1978) *A.B. Symp.* 12:165–178; Krogsgaard-Larsen et al. (1986) Benzodiazepine/GABA Receptors and Chroride Channels: Structural and Functional Properties, pp. 73–95).

B. Potentiators

Numerous compounds that potentiate the effects of GABA have been identified. Such compounds typically bind predominantly to sites other than the GABA binding site, such as, for example, the benzodiazepine site, the barbiturate or the steroid binding site.

Such potentiators include, but are not limited to, triazolopyridazine derivatives (see, e.g. WO 99/37649, WO 99/37648, and WO 99/37644), pyrazolo-pyridine derivatives (see, e.g. WO 99/48892), nicotinic carboxamide compounds (see, e.g., WO 99/43661 and U.S. Pat. No. 5,723,462), neuroactive steroids (see, e.g. WO 98/05337), such as, e.g., androstane derivatives and pregnane derivatives (see, e.g., U.S. Pat. No. 5,925,630), triazolophthalazine derivatives (see, e.g. WO 99/25353, and WO/98/04560), tricyclic pyrazolo-pyridazinone analogues (see, e.g. WO 99/00391), and fenamates (U.S. Pat. No. 5,637,617).

Compounds such as, e.g., barbiturates (e.g., pentobarbital) have also been shown to potentiate the effects of GABA. These compounds allow GABA to act efficiently are lower doses that those required to obtain a similar effect in the absence of the compound.

C. Antagonists

In addition, compounds that inhibit either the binding of GABA to the GABA$_A$ receptor or the GABA$_A$ receptor activity have also been isolated. Such antagonists include, e.g., thienobenzisoxazole derivatives (see, e.g. GB 2336589), triazolophthalazine derivatives, carboxamides (e.g., 5,6-Cycloalkano-fused 4-oxonicotinic, carboxamides), naphtho-imidazo (1,2-a) pyridine derivatives, N-substituted-4-oxo-4,5,6,7-tetrahydro-1H-indole-3-carboxamide derivatives, imidazodiazepine (Hunkeler et al. (1981) *Nature* 290:514–516), Bicuculline, RU5315, picrotoxin, pitrazepine, and the like (Krogsgaard-Larsen et al. (1986), supra).

III. USES OF THE COMPOUNDS OF THE INVENTION

The compounds of the present invention can be used to treat a number of diseases involving immune function. For example, GABA agonists are particularly useful for inhibiting the immune responses to treat a number of immune diseases such as, e.g., allergies, graft rejection, and autoimmune diseases, including, e.g., Systemic Lupus Erythematosus, Myasthenia Gravis, Rheumatoid Arthritis, Insulin Dependent Diabetes Mellitus, Multiple Sclerosis, and the like. In a preferred embodiment, the GABA$_A$ receptor agonists or potentiators are used to inhibit immune responses. In another preferred embodiment, the GABA$_A$ receptor antagonists of the invention are used to enhance TH1 cell-mediated immune responses. The compounds are typically administered peripherally (e.g., by oral, transdermal, intravenous, subcutaneous administration or by using a pump). In preferred embodiments, the compounds are unable to cross the blood-brain barrier and, therefore, do not affect the central nervous system.

A. Models for Autoimmune Diseases

The ability of the compounds of the present invention to treat autoimmune diseases can be assessed using a variety of well known models described herein. For example, animal models for Systemic Lupus Erythematosus, Myasthenia Gravis, Rheumatoid Arthritis, Insulin Dependent Diabetes Mellitus (see, below) and Multiple Sclerosis are known to those of skill in the art.

B. Graft Rejection

It has been shown that agents that block the ability of T cells to mount an immune response in humans effectively prevent or lessen graft rejection. In addition, studies of the process of graft rejection have shown that it is due to the antigen-specific activation of T lymphocytes, especially those bearing CD8 surface molecules. Inhibiting the T cell-mediated immune response therefore leads to greater tolerance of grafts. In one embodiment, the present invention provides a method for using the agonist compounds described herein to inhibit the Th1 cell-mediated immune response in order to increase graft survival. In another embodiment, the potentiators described herein are used in combination with the agonists of the present invention to inhibit the Th1 cell-mediated immune response.

The success of such a treatment can be assessed, for example, in mice, following grafting of a foreign tissue by measuring graft survival and adequate function of the allograft.

C. Models for Allergy

A wide variety of atopic or allergic disorders, commonly known as asthma or allergies, results from the effects of activating T cells. Such allergic disorders include, e.g., hay fever, extrinsic asthma, insect bite and sting allergies, food and drug allergies, allergic rhinitis, bronchial asthma, anaphylactic syndrome, urticaria, angioedema, atopic dermatitis, allergic contact dermatitis, erythema nodosum, erythema multiforme, Stevens-Johnson Syndrome, cutaneous necrotizing venulitis, bullous skin diseases, etc.

The ability of the compounds of the invention to reduce allergic reactions can be assayed using the murine model of OVA induced allergic asthma, in which mice are challenged with the OVA 323–339 epitope. The compounds of the invention can be administered, e.g., to OVA-sensitized mice before OVA challenge. Mice treated with the compounds of the invention are compared to mice treated with a control.

D. Enhancing TH1 Cell-mediated Immune Responses

As noted above, the GABA antagonists can be used to enhance Th1-mediated immune responses. TH1 cells produce IL-2, γ-interferon (γ-IFN), and lymphotoxin (LT), and mediate helper cell functions associated with cytotoxic T lymphocytes (CTLs), delayed-type hypersensitivity (DTH) and macrophage activation. IL-2 produced by Th1 cells plays a major role in the activation and differentiation of CTL precursors into mature CTL effectors.

Th1 cell-mediated immune response is generally more effective in fighting intracellular pathogens than other immune responses (such as, e.g., Th2-mediated immune response). Examples of infections in which Th1 cell-mediated immune appears to be more effective in fighting infection include, e.g., viral infections (such as, e.g., human immunodeficiency virus, Epstein-Barr virus), spirochetal infection (e.g.,syphilis), and protozoan infections, such as, e.g., cutaneous and visceral leishmaniasis.

The present invention provides a method to enhance Th-1 cells-mediated immunity by modulating the activity of the $GABA_A$ peripheral receptors using the $GABA_A$ receptors antagonists of the invention.

The ability of the compounds of the invention to enhance Th1 cells-mediated immune responses can be evaluated, for example, by measuring in mice the production of IL-2 or γ-IFN, using methods well-known to those of skill in the art.

IV. FORMULATION AND ADMINISTRATION

The complexes of the invention can be formulated to be administered to subjects in need thereof. Suitable formulations are found in Remington's *Pharmaceutical Sciences*, Mack Publishing Company, Philadelphia, Pa., 17th ed. (1985). A variety of pharmaceutical compositions comprising compounds of the present invention and pharmaceutically effective carriers can be prepared. The pharmaceutical compositions are suitable in a variety of drug delivery systems.

Pharmaceutically acceptable compositions of the compounds of the invention may be administered to a mammal (preferably, a human) in need of $GABA_A$ receptor-mediated immune response enhancement, potentiation or inhibition in dosages sufficient to modulate the immune response (an immunomodulatory amount). The dose will vary according to, e.g., the particular compound, the manner of administration, the particular disease being treated and its severity, the overall health and condition of the patient, and the judgment of the prescribing physician. Generally, this amount will be achieved in vivo at dosages of 0.01 to 250 mg/kg$^{-1}$, body weight, preferably 0.1 to 100 mg/kg$^{-1}$ and more preferably 1–20 mg/kg$^{-1}$, although skilled physicians will readily be able to adjust these dosages to achieve specific therapeutic ends.

Pharmaceutically acceptable compositions including the compounds of the invention, as well as salts and esters thereof, may be prepared as described herein. Pharmaceutically acceptable base salts include those formed from bases which form non-toxic base salts. These particular non-toxic base salts include, but are not limited to sodium, potassium, calcium, and magnesium. These salts can easily be prepared by treating the acidic compounds of the invention with an aqueous solution of the desired cation, and then evaporating the resulting solution to dryness, preferably while being placed under reduced pressure. Alternatively, pharmaceutically acceptable base salts may also be prepared by mixing lower alkanoic solutions of the acidic compounds and the desired alkali metal alkoxide together, and then evaporating the resulting solution to dryness in the same manner as described above. In either case, stoichiometric quantities of reagents are preferably employed in order to ensure complete reaction and maximum yield of the desired pharmaceutically acceptable base salts.

The pharmaceutical compositions are intended for intravenous, intramuscular, topical, oral or local administration, such as by aerosol, subcutaneously or transdermally, or by using a pump, for prophylactic and/or therapeutic treatment. The pharmaceutical compositions can be administered in a variety of unit dosage forms depending upon the method of administration. For example, unit dosage forms suitable for oral administration include powder, tablets, pills, and capsules.

For enteral administration the compounds of the invention can be administered in either single or multiple dosages. The compounds of the invention may be administered in combination with pharmaceutically acceptable carriers in a variety of dosage forms. For example, capsules, lozenges, hard candies, powders, sprays, aqueous suspension, elixirs, syrups, and the like may be formulated with various pharmaceutically acceptable inert carriers. Such carriers include solid diluents or fillers, sterile aqueous media and various non-toxic organic solvents. In general, the compounds of the invention will be included in oral dosage forms at concentration levels ranging from about 0.5% to about 90% by weight of the total composition, in amounts which are sufficient to provide the desired unit dosage.

Tablets may contain various excipients such as sodium citrate, calcium carbonate and calcium phosphate, along with various disintegrants such as starch (preferably potato or tapioca starch), alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

For parenteral use, the compounds of the invention may be formulated by means known in the art using suitable dispersing or wetting agents and suspending agents. A sterile injectable formulation can also be a solution of suspension in a non-toxic parenterally acceptable diluent or solvent, for example, as a solution in 1,3-butandiol. Among the acceptable vehicles and solvents are water, Ringer's solution and isotonic NaCl solution, fixed oils (including synthetic mono- or di-glycerides), fatty acids (such as oleic acids), and mixtures thereof.

For aerosol administration, the complexes are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1%–20% by weight of the composition, preferably 0.25–5%. The balance of the composition is ordinarily propellant. Liquefied propellants are typically gases at ambient conditions, and are condensed under pressure. Among suitable liquefied propellants are the lower alkanes containing up to 5 carbons, such as butane and propane, and preferably fluorinated or fluorochlorinated alkanes. Mixtures of the above may also be employed. In producing the aerosol, a container equipped with a suitable valve is filled with the appropriate propellant, containing the finely divided compounds and surfactant. The ingredients are thus maintained at an elevated pressure until released by action of the valve.

The compounds of the invention can also be administered in the form of liposomes. A variety of methods are available for preparing liposomes (see, e.g., Szoka et al. (1980) *Ann. Rev. Biophys. Bioeng.* 9:467; and U.S. Pat. Nos. 4,235,871, 4,501,728 and 4,837,028). One method produces multilamellar vesicles of heterogeneous sizes. In this method, the vesicle forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous solution of the targeted drug and the targeting component and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate. Compositions prepared in liposome form can contain stabilizers, preservatives, excipients, and the like in addition to the agent.

Additional pharmaceutical methods may be employed to control the duration of pharmacological action. Controlled release preparations may be achieved by the use of polymers to complex or adsorb the present active compounds. The controlled delivery may be exercised by selecting appropriate macromolecules (for example, polyesters, polyamino acids, polyvinyl pyrrolidone, ethylenevinylacetate, methylcellulose, carboxymethylcellulose, and protamine sulfate) and the concentration of macromolecules as well as the methods of incorporation in order to control release.

Another possible method to control the duration of action by controlled release preparations is to incorporate the active compound into particles of a polymeric material such as polyesters, polyamino acids, hydrogels, poly (lactic acid) or ethylene vinylacetate copolymers. Alternatively, instead of incorporating the active compounds into these polymeric particles, it is possible to entrap the active compounds in microcapsules prepared, for example, by coacervation techniques or by interfacial polymerization using, for example, hydroxymethylcellulose or gelatin-microcapsules and poly (methylmethacrylate) microcapsules, or in colloidal drug delivery systems, for example, liposomes, albumin microspheres, microemulsions, nanoparticles, and nanocapsules or in macroemulsions. Techniques for preparing such controlled release formulation are known to those of skill in the art and described, for example, in Remington (1985), supra.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight. The doses will generally be in the ranges set forth above.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

V. EXAMPLES

Example 1

GABA INHIBITS ANTI-CD3 STIMULATED T CELL PROLIFERATION

When naive T cells recognize a peptide/MHC complex via their T cell TCR/CD3 complex, they activate and differentiate into effector cells and proliferate, expanding the antigen-reactive T cell pool (Janeway and Bottomly (1994) Cell 76:275–285). Anti-CD3 can mimic this interaction and polyclonally activate T cells. As an initial screen for an immunoregulatory action by GABA, anti-CD3 induced T cell proliferation wasassayed in the presence of GABA.

To determine mitogen stimulated T cell proliferation, mononuclear splenic cells ($3 \times 10^5$/well) from naive mice were incubated with 1 μg/ml anti-CD3 (2c11 clone, Pharmingen) in the presence or absence of GABA (Sigma, St. Louis) for 48 hours. The data are presented as the mean percent $^3$H-thymidine incorporation relative to the positive control from groups of 5–6 mice which were tested in 2–3 independent experiments.

Splenic mononuclear cells from six-eight weeks-old naive BALB/c mice (Jackson Laboratory) which were treated with anti-CD3 proliferated 100 fold more than control cells which were not stimulated with anti-CD3. In the presence of GABA, the anti-CD3 induced T cell proliferative response was significantly reduced—e.g., at 300 μM GABA, the anti-CD3 stimulated proliferation was 60% that of CD3 stimulated cultures without GABA (FIG. 1).

GABA itself (without anti-CD3) failed to stimulate T cell proliferation and had little impact on T cell survival in our experimental system. In addition, 10 μM-10 mM GABA did not significantly affect the T cell response to PMA and ionomycin. These data indicate that naive T cells express GABA receptors and that the inhibition of T cell proliferation by GABA may occur through the TCR/CD3 complex-gated signal pathway.

Example 2

GABA INHIBITS T CELL RESPONSES TO FOREIGN AND SELF-ANTIGENS

To further test the possibility that GABA exerts an inhibitory effect on T cell proliferation through the TCR/CD3 signal pathway, the impact of GABA on T cell recall responses to foreign antigens was examined.

Figure 2:
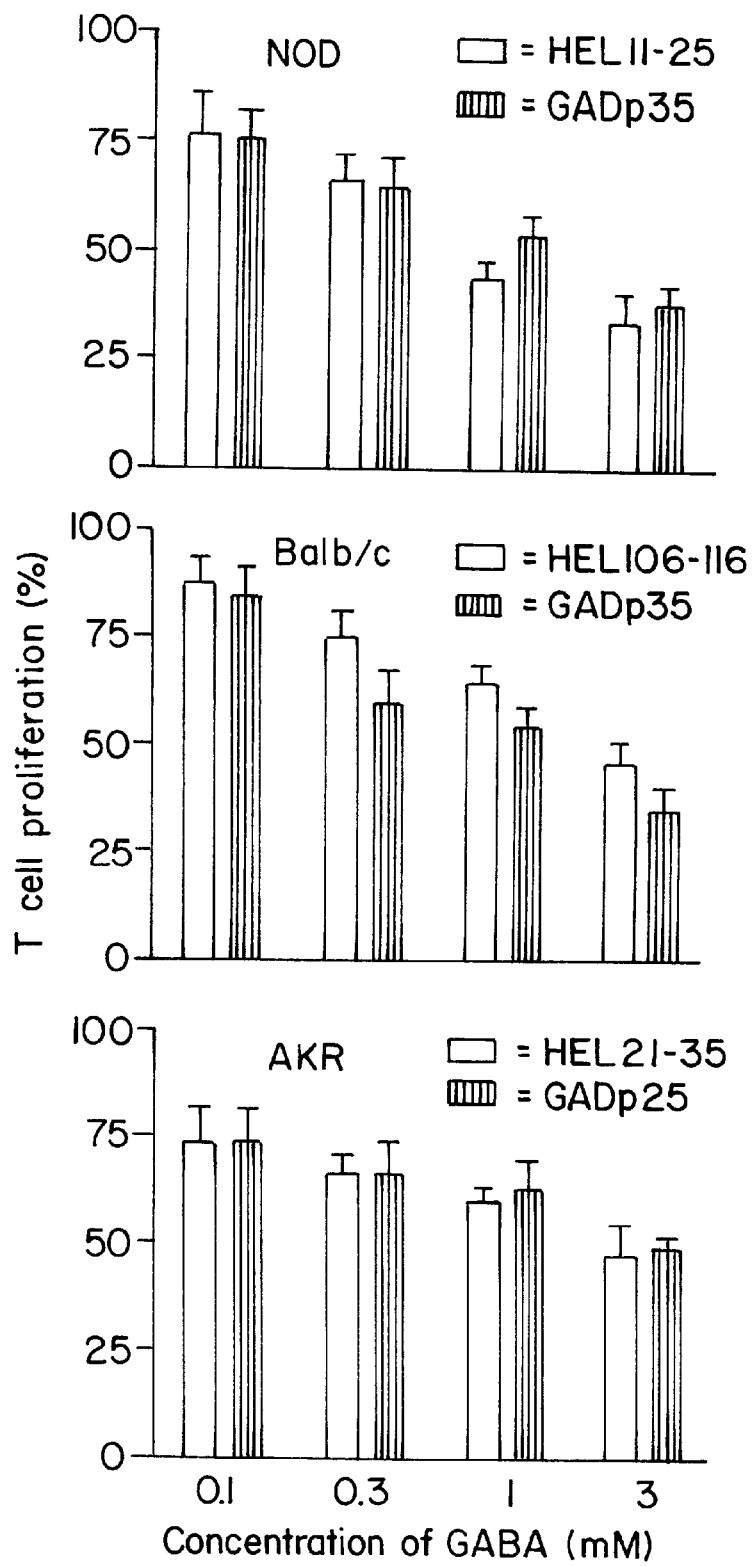
FIG. 2 shows that GABA inhibits lymph node T cell recall responses to antigen. NOD, Balb/c and AKR mice were immunized with an immunogenic foreign (HEL) or self (GAD) peptide in 50% CFA. The influence of GABA on lymph node T cell responses to the injected antigen was analyzed using a proliferation assay. The data are presented as the per cent $^3$H-thymidine incorporation relative to control antigen stimulated cells (without GABA—which ranged from an average of 49,881–60,472 cpm between the three strains of mice). For all three strains, the background of $^3$H-thymidine incorporation in cultures with medium alone or GABA alone 2,014–3,322 cpm). Groups of 5 mice were tested in two independent experiments.

Three strains of mice with different MHC class II alleles were immunized with an immunogenic peptide from hen egg lysozyme (HEL). Hen egg lysozyme peptides $HEL_{11-25}$, $HEL_{106-116}$ and $HEL_{21-35}$ served as immunogenic foreign-antigen determinants for six-eight week-old NOD (Taconic Farms), Balb/c and AKR mice (Jackson Laboratory), respectively (Deng et al. (1993) J. Exp. Med. 178:1675–1680; Moudgil and Sercarz (1993) J. Exp. Med. 178:2131–2128; Cabaniols et al. (1994) Eur. J. Immunol. 24:1743–1749). Mice were injected with 20 nM peptide in 50% complete Freund's adjuvant (CFA, Gibco) in their hind food-pad. Nine days later, lymph node mononuclear cells were isolated and $3 \times 10^5$ mononuclear cells/well were re-exposed in vitro to the injected peptide (7 μM) and tested in triplicate for recall responses in the presence of different concentrations of GABA. GABA was shown to inhibit T cell proliferation to the immunogens in a dose-dependent manner in all three strains of mice tested (FIG. 2).

The ability of GABA to inhibit T cell recall responses to self-antigens was also examined. GAD peptides were selected from an overlapping set of peptides which span the GAD molecule (Atkinson et al. (1994) J. Clin. Invest. 94:2125–2129). GAD65 peptide 35 (GADp35) contains a self-antigen determinant for NOD ($H-2^{NOD}$; Taconic Farms) and BALB/c ($H-2^d$) mice (Jackson Laboratory) and GAD peptide 25 (GADp25) contains a self-antigen determinant for AKR ($H-2^k$) mice (Jackson Laboratory; Kaufman et al. (1993) Nature 366:69–72). Following immunization with 20 nM of immunogenic GAD peptide in 50% complete Freund's adjuvant (CFA, Gibco), T cell proliferation was assayed as described above. GABA was shown to inhibit proliferative T cell responses to the injected antigen in all three strains of mice in a dose-dependent manner (FIG. 2). GABA thus inhibits T cell proliferative recall responses to both foreign and self-antigens in vitro.

Example 3

GABA INHIBITS IL-2 PRODUCTION FOLLOWING ANTIGEN CHALLENGE

Activated T cells respond to their cognate antigen by secreting cytokines which promote clonal expansion through autocrine positive feedback (Paul and Seder, 1994). Administering antigen in CFA generally primes antigen-specific Th1 responses whose proliferation relies on the concentration of IL-2. To understand the mechanism(s) underlying GABA inhibition of T cell proliferative responses, the ability of GABA to inhibit IL-2 production by activated antigen-specific T cells was determined.

Mice (6–8 weeks in age) were injected with 20 nM GADp35 peptide in 50% complete Freund's adjuvant (CFA, Gibco) in their hind food-pad. Nine days following immunization, lymph node mononuclear cells were isolated and five million mononuclear cells/ml were cultured with the injected peptide (at 2, 7 and 20 micromolar) without, or with different concentrations of GABA, in vitro for 36 hours to stimulate IL-2 production. The supernatant of the cultured cells was harvested and the activity of IL-2 was measured using the IL-2-dependent cell line CTLL-2. Recombinant mouse IL-2 (Genzyme) was used as a standard.

Figure 3:
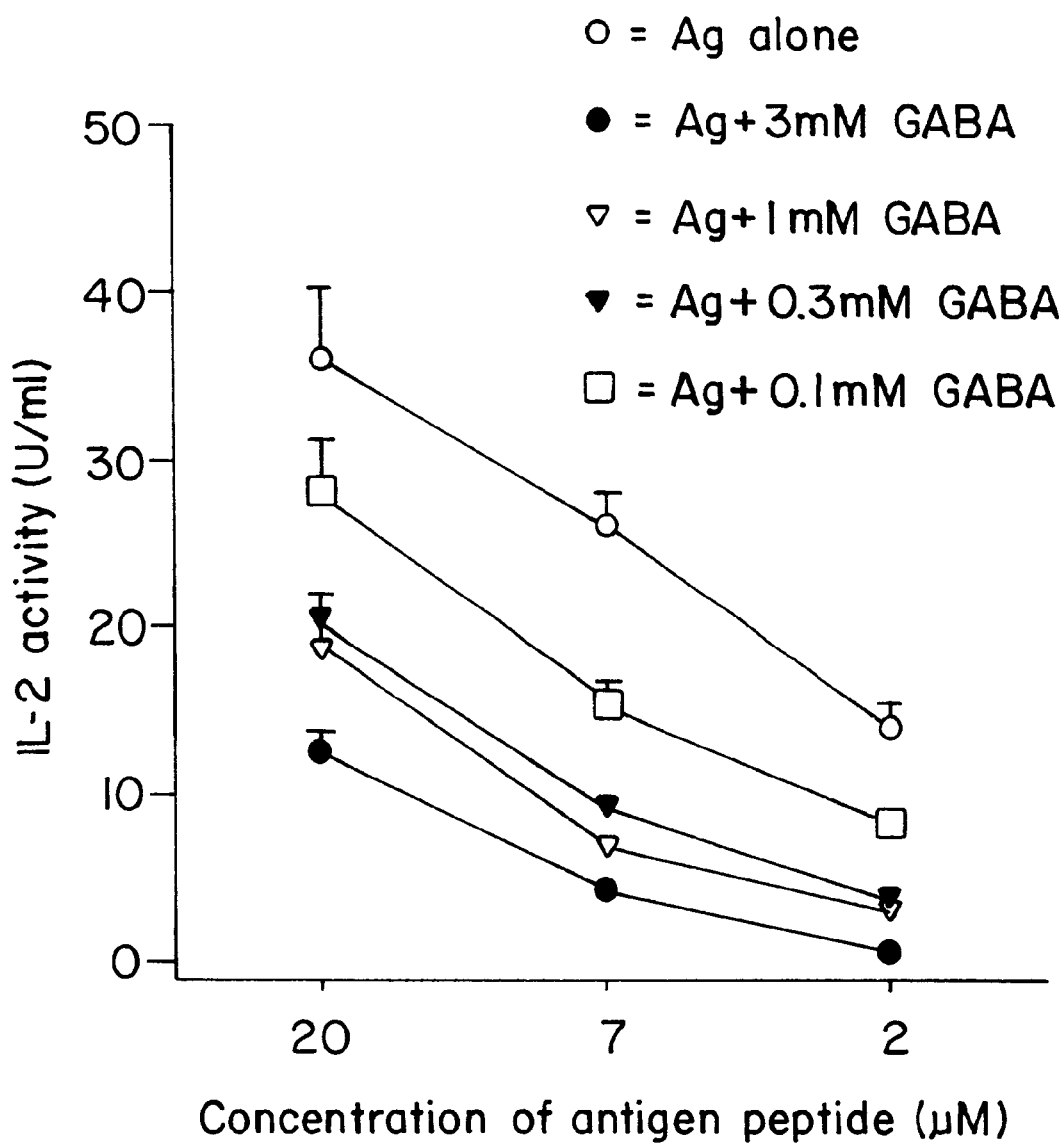
FIG. 3 shows that GABA inhibits IL-2 production by antigen stimulated T cells. Lymph node mononuclear cells ($5 \times 10^6$/ml) from GADp35 immunized NOD mice were cultured with GABA in a range of concentrations and challenged with different concentrations of the injected peptide for 36 hours to stimulate IL-2 production. The IL-2 activity in supernatant was determined by IL-2-dependent CTLL proliferation. The data are expressed as IL-2 units/ml±SD. Recombinant mouse IL-2 (0.8–50 units/ml) was used as a standard and showed a linear relationship with CTLL proliferation.

These experiments showed that in the presence of GABA, antigen-induced IL-2 secretion was reduced in a dose-dependent manner. For example, at 0.3 mM GABA, IL-2 activity in cultured supernatants was reduced to 55–31% of that in supernatants from control cultures (containing the same concentration of peptide but no GABA; FIG. 3). Control CTLL-2 cell responses to recombinant murine IL-2 were unaffected by the addition of GABA (10 μM-10 mM), indicating that GABA did not directly interfere with their response to IL-2. Together, these data suggest that the GABA-mediated immuno-suppression appears to act through inhibition of IL-2 production by primed T cells in response to an antigen challenge, rather than through inhibition of the IL-2 receptor signal pathway.

Example 4

$GABA_A$ RECEPTORS MEDIATE THE IMMUNO-SUPPRESSIVE EFFECT OF GABA

The effects of GABA are mediated through at least two receptors, the $GABA_A$ and $GABA_B$ receptors. Various receptor-specific agonists and antagonists were used to determine which receptor mediated the immuno-inhibitory effects of GABA. The effect of these agonists and antagonists was evaluated by measuring both anti-CD3 and antigen-induced T cell proliferation.

To determine the mitogen stimulated T cell proliferation, mononuclear splenic cells ($3 \times 10^5$/well) from naive mice were incubated with 1 μg/ml anti-CD3 (2c11 clone, Pharmingen) or 500 ng/ml ionomycin (A23187, Sigma, St. Louis) and 5 ng/ml phorbol 12-myristate 13-acetate (PMA, Sigma, St. Louis) in the presence or absence of GABA and of an agonist or antagonist (Sigma, St. Louis) for 48 hours.

To assay the effect on T cell proliferation of different GABA receptor-specific agonists or antagonists, mice were injected with 20 nM immunogenic peptide in 50% complete Freund's adjuvant (CFA, Gibco) in their hind food-pad. Nine days later, lymph node mononuclear cells were isolated and $3 \times 10^5$ mononuclear cells/well were exposed to different concentrations of GABA receptor-specific agonists or antagonists and then challenged with the injected peptide (7 $\mu$M) in triplicate to test proliferative recall responses.

Figure 4:
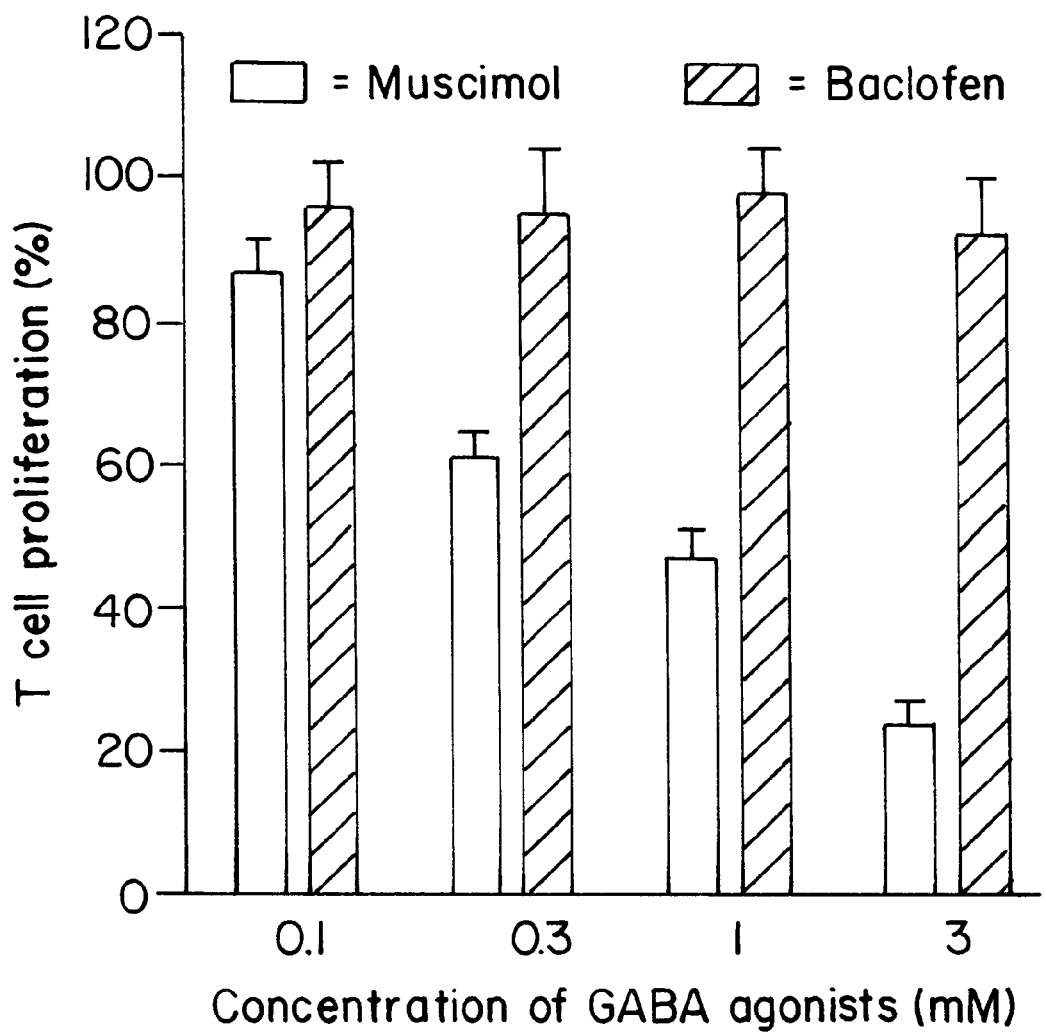
FIG. 4 shows that muscimol, but not baclofen, inhibits antigen primed T cell proliferation. Lymph node mononuclear cells from GADp35 primed NOD mice were pretreated with different concentrations of muscimol or baclofen in vitro, and then challenged with 7 $\mu$M GADp35 to stimulate antigen specific T cell proliferation. The data are presented as the per cent $^3$H-thymidine incorporation relative to control peptid-estimulated cells without muscimol or baclofen treatment. Lymph node mononuclear cells in medium alone served as negative controls. Cells treated with muscimol or baclofen alone had a similar level of $^3$H-thymidine incorporation as the negative controls. Similar results were obtained using lymph node mononuclear cells from Balb/c mice. Groups of 5–6 mice were tested in two independent experiments.
Figure 5:
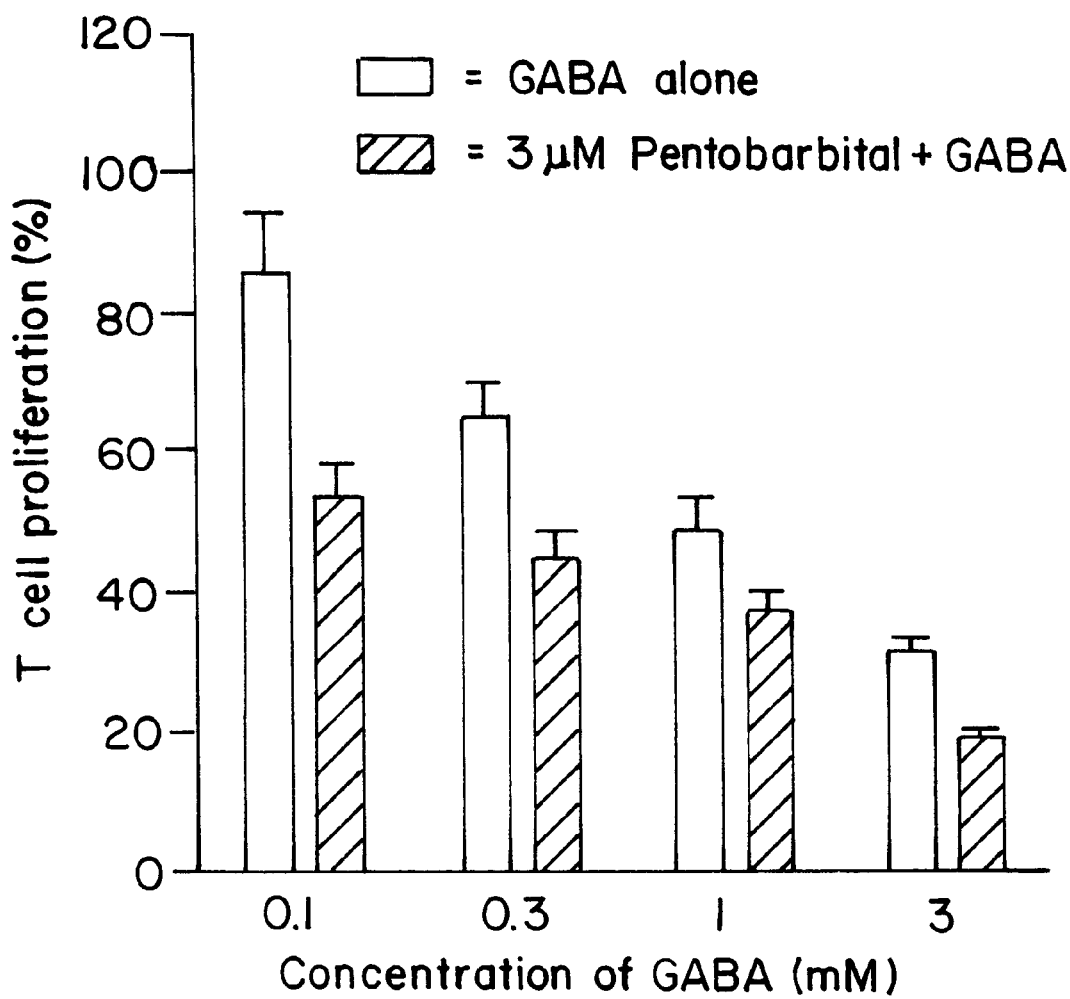
FIG. 5 show that pentobarbital enhances the inhibitory effect of GABA on T cell proliferation. Lymph node mononuclear cells from GADp35 immunized NOD mice were cultured with 3 $\mu$M pentobarbital together with different concentrations of GABA and then challenged with 7 $\mu$M GADp35 for 96 hours. The data are presented as the per cent $^3$H-thymidine incorporation relative to control antigen-stimulated cells without any drug treatment (63,780–70,290 cpm). Cells treated with 3 $\mu$M pentobarbital in medium had a level of $^3$H-thymidine incorporation similar to that of medium alone. 3 $\mu$M pentobarbital (without GABA) had little impact on antigen-primed T cell proliferation. Similar results were obtained using lymph node mononuclear cells from Balb/c mice. Groups of 5 mice were tested in three independent experiments.

Muscimol (Sigma, St. Louis), a $GABA_A$ receptor agonist, was shown to inhibit in a dose-dependent manner both anti-CD3 and antigen-induced T cell proliferation—for example, at 300 $\mu$M muscimol reduced antigen primed T cell responses by approximately 40% (FIG. 4). In contrast, addition of baclofen (10 $\mu$M-10 mM; Sigma, St. Louis), a $GABA_B$ receptor agonist, had little effect on T cell proliferation (FIG. 4) and did not interfere with the immuno-suppressive action of muscimol. Furthermore, 3 $\mu$M pentobarbital potentiated the actions of GABA, causing a greater inhibition of T cell responses (FIG. 5). These data indicate that $GABA_A$, but not $GABA_B$, receptors mediate the inhibition of T cell responses.

Figure 6:
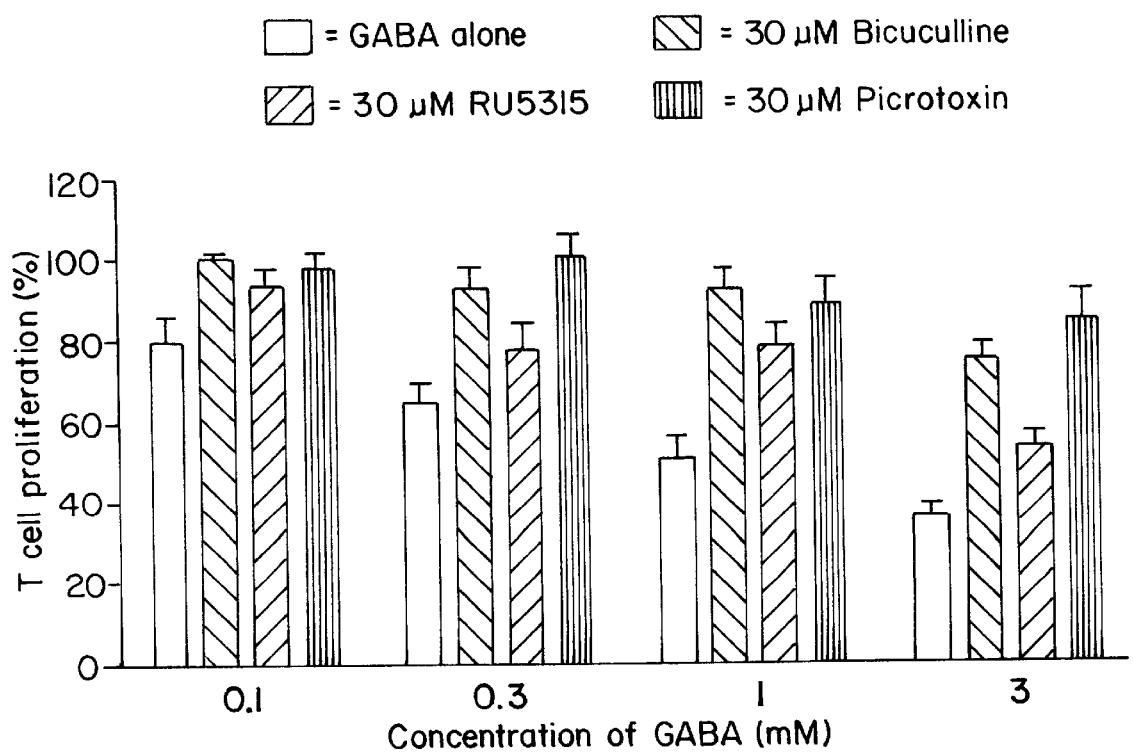
FIG. 6 shows that $GABA_A$ receptor antagonists block the immuno-inhibitory effect of GABA. Lymph node mononuclear cells from NOD mice which were immunized with GADp35 were cultured with bicuculline, RU5135 or picrotoxin. The cells were exposed to different concentrations of GABA and then challenged with GADp35 to determine the effect of the drugs on T cell proliferation. The data are expressed as the per cent $^3$H-thymidine incorporation relative to control antigen-stimulated cells without any drug treatment. Medium alone served as the negative control ($\approx$1,800–2,400 cpm). The antagonists alone failed to stimulate cell proliferation and showed little effect on T cell responses to antigen. Groups of 5–6 mice were tested in three independent experiments. Similar results were obtained using Balb/c mice.

The immuno-inhibitory effect of GABA was greatly reduced by co-incubation with the $GABA_A$ competitive antagonists bicuculline (Sigma, St. Louis) or RU5315 (UCLA), and was almost abolished by co-incubation with picrotoxin (a non-competitive antagonist and Cl⁻ channel blocker; Sigma, St. Louis), even in the presence of high concentrations of GABA (FIG. 6). These drugs also antagonized the immuno-inhibitory effect of muscimol. In contrast, co-incubation with 1 $\mu$M-1 mM strychnine (a glycine receptor antagonist (Sigma, St. Louis; Ling et al. (1993) *J. Appl. Physiol.* 74:1265–1273), 1 $\mu$M-500 $\mu$M γ-vinyl-GABA (a GABA transaminase inhibitor; UCLA; Neal and Shah (1990) *Br. J. Pharmacol.* 100:324–328) and 1 $\mu$M-500 $\mu$M nipecotic acid (an inhibitor of GABA reabsorption; Sigma, St. Louis; Isaacson et al. (1993) *Neuron* 10:165–175) did not significantly affect the GABA-mediated inhibition of T cell proliferation. Furthermore, 10 $\mu$M-10 mM β-alanine and glutamic acid alone (Sigma, St. Louis), or co-incubated with GABA, had little effect on T cell proliferative responses.

These data pharmacologically demonstrate the presence of functional $GABA_A$ receptors on T cells which mediate the immuno-suppressive effects of GABA. Furthermore, these lymphocytic $GABA_A$ receptors can be manipulated pharmacologically in a manner similar to neuronal $GABA_A$ receptors.

Example 5

GABA INHIBITS ANTIGEN-PRIMED DTH INFLAMMATORY RESPONSES

To determine whether GABA could modulate immune responses in vivo, a placebo pellet or a pellet designed to consistently release GABA over a 21 day period (maintaining a serum level of approximately 300 $\mu$M GABA) was implanted in mice, and their ability to mount recall responses to antigen in a standard DTH assay was then determined.

Ten weeks old female NOD mice (Taconic Farms) were implanted with a pellet under the skin of their neck which was designed to release 600 $\mu$g/day GABA over a 21 day period (Innovative Research of America, Sarasota, Fla.). Control mice were implanted with a placebo pellet which did not contain GABA. The next day, the mice were immunized with 100 $\mu$g keyhole limpet hemocyanin (KLH, Sigma), a prototypic foreign antigen, in 50% CFA at the base of their tail. One week later, the mice were challenged with KLH (100 $\mu$g in 25 $\mu$l PBS) in their right footpad, while the left footpad received ovalbumin (100 $\mu$g in 25 1 PBS) as a control. Both hind feet were measured before injection and at 24, 48, 72 and 96 hrs post injection using a monostat caliper. Footpad swelling was expressed as the average size increase (in millimeters) of the KLH-injected footpad compared to the control ovalbumin-injected footpad of each animal. The measurements were conducted in a blinded fashion on coded animals.

Figure 7:
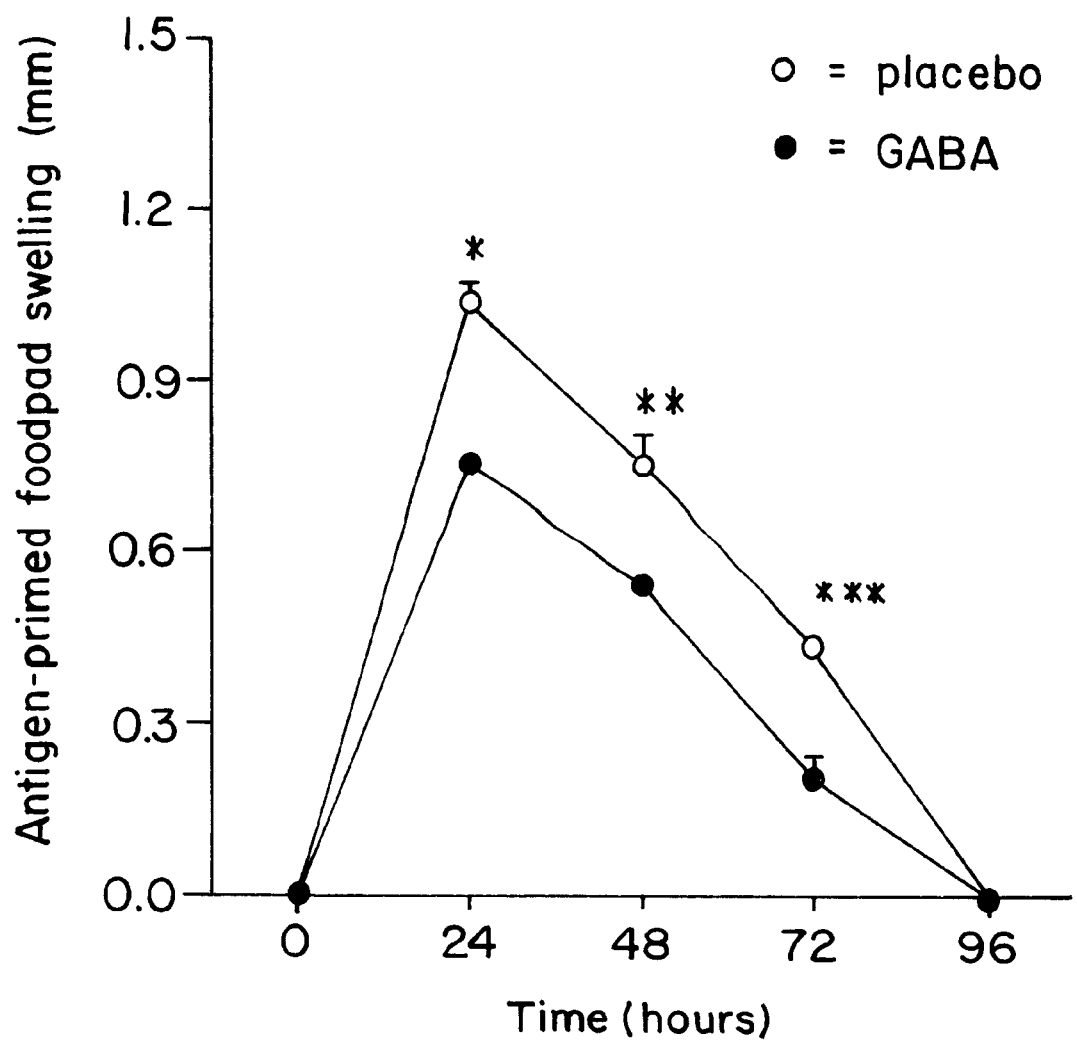
FIG. 7 shows that GABA inhibited antigen-primed DTH responses. NOD mice were implanted with either a pellet designed to release 600 $\mu$g GABA/day, or a placebo pellet under the skin of their neck. The next day, the mice were immunized with KLH in 50% CFA at the base of their tail. One week later, the mice were challenged with KLH in PBS in their right footpad, while the left footpad received ovalbumin in PBS as a control. Footpad swelling was expressed as the average size increase of the KLH injected footpad compared to the control footpad±SD (n=5 mice/group, *p<0.005, p<0.002, *p<0.001). Both GABA and placebo pellet treated groups did not display significant DTH responses to ovalbumin. There were no obvious signs of toxicity in mice implanted with GABA-releasing pellets.

The size of the ovalbumin-injected footpads of both GABA and placebo treated mice remained near to baseline values. In contrast, the KLH-injected footpad of both GABA and placebo pellet treated animals displayed DTH responses which peaked at around 24 hours and declined to base-line values by 96 hours post-injection. However, the KLH-injected footpads of mice implanted with a GABA-releasing pellet displayed significantly less swelling. Throughout the 24–72 hour response period, GABA-treated mice had on average 30–50% less footpad swelling in response to KLH than placebo-treated mice (FIG. 7, $p < 0.005$). Thus, GABA inhibited T cell-mediated DTH responses in vivo.

Example 6

GABA INHIBITS IDDM IN NOD MICE

Nonobese diabetic (NOD) mice, which spontaneously develop insulitis at 4 weeks of age and IDDM by 4–6 months of age (Delovitch, et al. *Immunity* 7:727–38 (1997)) were used to determine the effects of GABA on IDDM. A NOD strain congenic for the severe combined immunodeficiency (scid) mutation developed to study diabetogenesis in NOD mice was used in the adoptive transfer experiment. Neither insulitis nor diabetes is observed in the NOD-scid mice because they lack functional lymphocytes. This ensured that the T cells responsible for diabetes in recipient NOD-scid mice were derived from the diabetic donor NOD mice. Only female NOD mice were used since they incur a higher incidence of IDDM than males.

To examine whether GABA administration could inhibit the adoptive transfer of disease to recipient mice, ten to twenty million splenocytes from NOD mice with a recent onset of IDDM were intravenously injected into recipient NOD-scid mice at 6 weeks of age. Prior to receiving the inject-ions, recipient mice were implanted with either a 21-day or a 60-day slow release GABA pellet under the skin of their back. This pellet was designed to consistently release GABA (600 $\mu$g/day) over the desired period (i.e. 21 or 60-day). The control mice received a placebo pellet instead the GABA pellet. The mice were monitored for diabetes onset by testing their urine glucose levels with Tes-tape and blood glucose levels with a glucometer. The onset of IDDM is defined as two consecutive blood glucose readings of over 300 mg/dl.

In mice receiving the 21-day slow release pellets, the controls that received the placebo pellet developed IDDM within 4 weeks of transfer. In contrast, mice that received the GABA pellet had a significantly reduced diabetes incidence and those that did develop IDDM showed a delayed onset of the disease.

Figure 8:
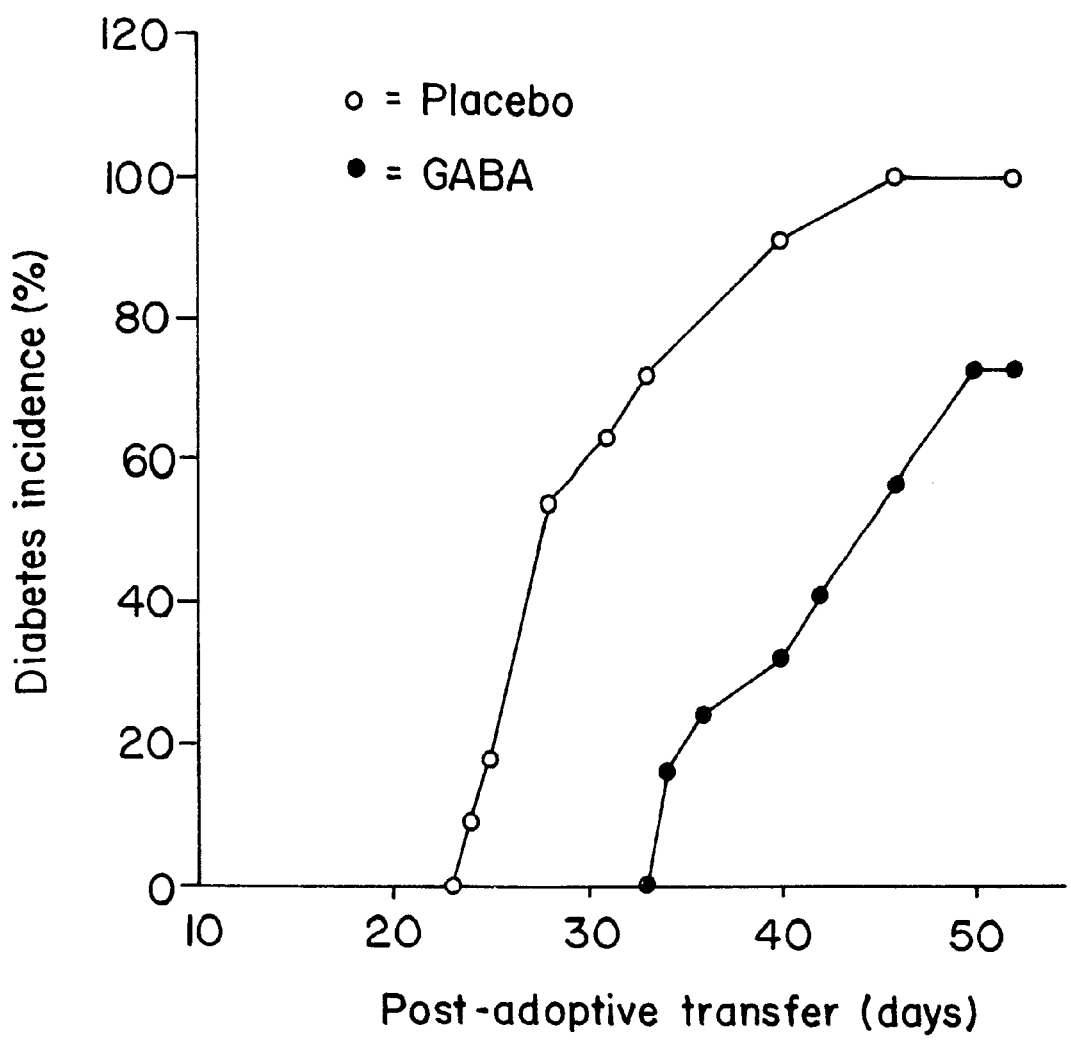
FIG. 8 shows that GABA inhibits the adoptive transfer of IDDM to NOD-scid mice. Ten to twenty million splenocytes from NOD mice with recent onset of IDDM were intravenously injected into recipient 6-week-old mice. Prior to injection, mice were implanted with either 21-day slow release GABA or placebo pellets. (n=12 for both groups).

As for the 60-day slow release pellets, the placebo group developed diabetes at the same time as mice given the 21-day placebo pellets. The 60-day experimental group had a delayed onset of IDDM beginning at 7 weeks whereas the 21-day GABA pellet recipients had a delayed onset of disease beginning at 4 weeks (FIG. 8). Gaba inhibits antigen-primed dth inflammatory responses.

Administration of GABA in vivo, thus inhibits the adoptive transfer of IDDM to NOD-scid mice.

What is claimed is:

1. A method of inhibiting an immune response in a patient, the method comprising administering an immunomodulatory amount of a GABA agonist.

2. The method of claim 1, wherein the compound is administered intravenously, transdermally, subcutaneously, or orally.

3. The method of claim 1, wherein the immune response is associated with an autoimmune disease.

4. The method of claim 3, wherein the autoimmune disease is insulin dependent diabetes mellitus.

5. The method of claim 3, wherein the immune response is associated with an allergic response.

6. The method of claim 3, wherein the immune response is associated with graft rejection.

7. The method of claim 3, wherein the GABA agonist is muscimol.

8. The method of claim 3, further comprising administering a GABA potentiator.

9. The method of claim 8, wherein the GABA potentiator binds to the benzodiazepine binding site within a $GABA_A$ receptor.

* * * * *